United States Patent
Hasbani et al.

(10) Patent No.: US 11,906,505 B2
(45) Date of Patent: Feb. 20, 2024

(54) METHOD OF DETERMINING RENEWABLE CARBON CONTENT WHILE PRODUCING AND BLENDING BIOGENIC-BASED FUELS OR BLENDSTOCKS WITH FOSSIL FUEL IN A REFINING OR BLENDING FACILITY

(71) Applicant: CHEVRON U.S.A. INC., San Ramon, CA (US)

(72) Inventors: Meir R. Hasbani, El Segundo, CA (US); Michelle K. Young, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/668,463

(22) Filed: Feb. 10, 2022

(65) Prior Publication Data

US 2022/0276218 A1    Sep. 1, 2022

Related U.S. Application Data

(60) Provisional application No. 63/148,769, filed on Feb. 12, 2021.

(51) Int. Cl.
| | | |
|---|---|---|
| *C10L 1/04* | (2006.01) | |
| *G01T 1/20* | (2006.01) | |
| *G01N 33/28* | (2006.01) | |

(52) U.S. Cl.
CPC ............ *G01N 33/2882* (2013.01); *C10L 1/04* (2013.01); *G01T 1/20* (2013.01);
(Continued)

(58) Field of Classification Search
CPC ....... H01L 2224/48091; H01L 2224/49; H01L 2224/49109; H01L 2224/49171; H01L 24/49; H01L 2924/14; H01L 2924/00012; H01L 2924/00014; C10G 2300/4037; C10G 3/40; C10G 3/42; C10G 3/50; C10L 1/04;
(Continued)

(56) References Cited

U.S. PATENT DOCUMENTS

| | | |
|---|---|---|
| 9,671,384 B2 | 6/2017 | Rogel et al. |
| 2010/0076238 A1* | 3/2010 | Brandvold ................ C10L 1/08 585/324 |

(Continued)

FOREIGN PATENT DOCUMENTS

WO    2014001633 A1    1/2014

OTHER PUBLICATIONS

Norton, Glenn A., et al., Use of radiocarbon analyses for determining levels of biodiesel in fuel blends—Comparison with ASTM Method D7371 for FAME, www.elsevier.com/locate/fuel, Feb. 5, 2012, 7 pages.

(Continued)

*Primary Examiner* — Ellen M McAvoy
*Assistant Examiner* — Chantel Graham

(57) ABSTRACT

A method of monitoring renewable carbon in fuel streams in a refinery or blend facility while co-processing a bio-feedstock with a fossil feedstock or blending a renewable product with a fossil product wherein the method provides for quantification of renewable C14 carbon content to adjust the total renewable content to a targeted renewable content in situ while lowering the limit of detection.

18 Claims, 3 Drawing Sheets

(52) U.S. Cl.
CPC ............ *C10G 2300/4037* (2013.01); *C10L 2200/0407* (2013.01); *C10L 2200/0476* (2013.01); *C10L 2290/60* (2013.01)

(58) Field of Classification Search
CPC ..... C10L 2200/0407; C10L 2200/0476; C10L 2290/60; G01N 33/2882; G01T 1/20
See application file for complete search history.

(56) References Cited

U.S. PATENT DOCUMENTS

| | | |
|---|---|---|
| 2014/0288338 A1 | 9/2014 | Radlein et al. |
| 2019/0249101 A1* | 8/2019 | Ohler ..................... C10L 1/04 |
| 2020/0181502 A1 | 6/2020 | Paasikallio et al. |

OTHER PUBLICATIONS

Manser, Rosy, et al., Machine learning approaches for easy and precise image segmentation, Carl Zeiss Microscopy GmbH, Germany, Zeiss Zen Intellesis, Jul. 2018, 8 pages.

Reddy, Christopher M., et al., Determination of Biodiesel Blending Percentages Using Natural Abundance Radiocarbon Analysis: Testing the Accuracy of Retail Biodiesel Blends, Environ. Sci. Technol. 2008, 42, 2476-2482, 7 pages.

Perkins, Joseph, et al., Automated image analysis techniques to characterise pulverised coal particles and predict combustion char morphology, Faculty of Engineering, University of Nottingham, www.elsevier.com/locate/fuel, Fuel 259 (2020) 116022, UK, 9 pages.

Kristof, Romana, et al., Liquid Scintillation Spectrometry as a Tool of Biofuel Quantification, Research Gate Chapter Jan. 2017, DOI: 10.5772/65549, 14 pages.

PCT International Search Report and Written Opinion re PCT/IB2022/051183, dated May 6, 2022, containing 14 pages.

* cited by examiner

METHOD OF DETERMINING RENEWABLE CARBON CONTENT WHILE PRODUCING AND BLENDING BIOGENIC-BASED FUELS OR BLENDSTOCKS WITH FOSSIL FUEL IN A REFINING OR BLENDING FACILITY

BACKGROUND OF THE INVENTION

Many states and the U.S. EPA encourage the use of cleaner low-carbon fuels and encourage the production of these fuels, and therefore, reduce greenhouse gas emissions. For example, in California under the Low Carbon Fuel Standard (LCFS), the carbon intensity (CI) scores assessed for each fuel are compared to a declining CI benchmark for each year. Low carbon fuels below the benchmark generate credits, while fuels above the CI benchmark generate deficits. Providers of transportation fuels must demonstrate that the mix of fuels they supply for use in California meets the LCFS CI standards, or benchmarks, or purchase credits to make up the difference for each annual compliance period.

One way for producing cleaner fuels while using current resources is by co-processing. More specifically, co-processing refers to the simultaneous transformation of biogenic feedstocks or low CI non-biogenic feedstocks and intermediate petroleum distillates such as vacuum gas oil (VGO) in existing petroleum refinery process units to produce low carbon fuels. To generate credits, California Air and Resources Board (CARB) and EPA pathways require determination of 1) the amount of renewable fuel produced, and 2) energy used to create renewable fuel. However, the complexity involved in co-processing and blending biogenic feedstocks, in facilities which also process and/or blend petroleum feedstocks creates challenges in tracking, monitoring, and verification of renewable fuels produced.

SUMMARY OF THE INVENTION

Herein is described a method for measuring the amount of C14 present in hydrocarbon fuels and their blend streams in refinery coprocessing operations by 1) providing fixed sampling points within the petroleum coprocessing operation between input of bio feedstock to select product outputs and 2) analyzing the samples collected with a triple to double coincidence ratio (TDCR) scintillation counter. An embodiment of the invention is the use of fixed sampling points to reduce the total number of downstream measurements typically required when determining bio-based carbon content in a refinery co-processing petroleum and bio-based feedstocks. A further embodiment is 90% or greater of the renewable carbons are accounted for with a detection limit from about 0.7 to about 2.0 wt % for bio-based carbon content.

A further embodiment of the invention is a method of adjusting renewable carbon content by measuring the amount of C14 present in hydrocarbon fuels and their blend streams in any coprocessing or fuels blending operation by 1) providing fixed sampling points within the petroleum coprocessing or biofuels blending operation between input of bio feedstock to select product outputs and 2) analyzing the samples in situ collected using C14 analysis, 3) determining the total renewable content from the collected samples and 4) adjusting the determined renewable content by blending with a renewable carbon source or by increasing the biofuel coprocessing rate. A further embodiment of the invention is utilizing C14 measurement at strategic points in refineries or blend facilities wherein renewable and petroleum products are processed singularly or in combination to produce a final biofuel product with a maximized C14 content.

DETAILED DESCRIPTION AND CLAIMS

Figure 1:
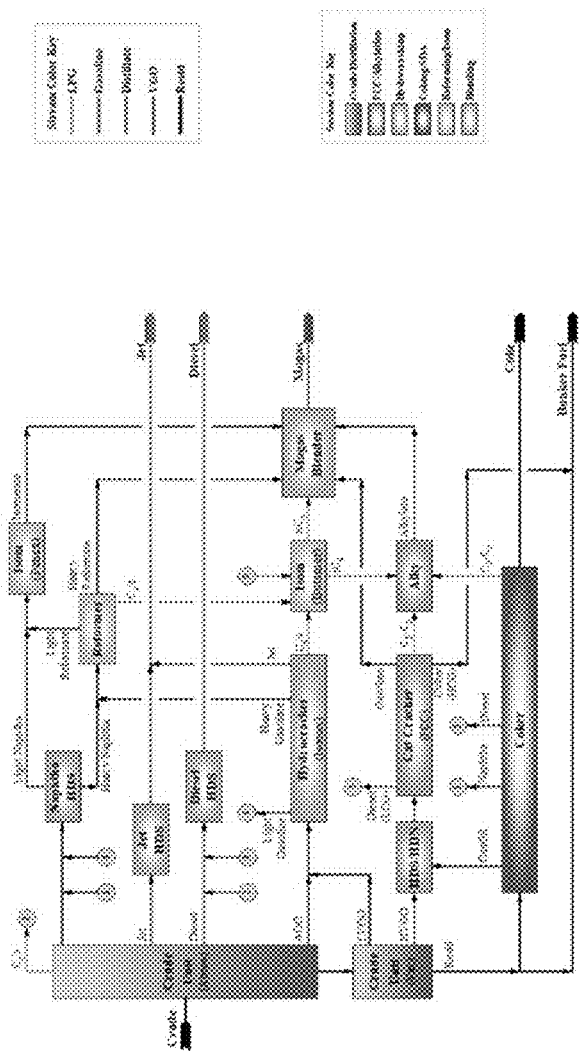
FIG. 1 is a schematic of a typical petroleum-based fuels refinery.

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

Two options commonly considered for tracking renewable components during processing are 1) $^{14}C$ carbon isotope analysis of feedstocks and products, and 2) total mass balance method based upon complete conservation of mass of the feedstocks and petroleum intermediates.

Modern oil refineries are typically large, sprawling industrial complexes with extensive piping running throughout, carrying feedstocks and product streams between large refining units. Such complexity of refining units makes tracking renewable carbons and determination of mass balance between biogenic feedstocks, intermediate and fuels during co-processing almost impossible.

Radiocarbon, also known as $^{14}C$, is a radioactive isotope of carbon that is continuously generated in the upper layer of the troposphere by thermal neutron absorption by nitrogen atoms. Radiocarbon has a half-life of 5,730 years, and the equilibrium condition between the uptake rates and the decaying rates makes the concentration of $^{14}C$ in the living matter is considered stable. And hence, radiocarbon analysis is considered most viable quantification method for distinguishing between bio-based carbon and fossil carbon by measuring the ratio of $^{14}C$ and $^{12}C$ isotope in the sample. Accelerator mass spectrometry (AMS) is the most precise technique, and the ASTM D6866-18 is the standard method commonly used to determine bio-based content in solid, liquid, and gaseous samples using Radiocarbon $^{14}C$ analysis. However, long analysis times, instrument cost, and tedious sample preparation methods make AMS technique, and ASTM standard D6866-18 methods unsuitable for implementing the technique in the refinery. A robust accounting method for renewable fuels and component quantification in refinery streams and products is therefore desired.

Definitions

"Co-processing" as used herein refers to the simultaneous transformation of biogenic feedstocks and intermediate petroleum distillates through petroleum refinery process units including but not limited to fluid catalytic cracking (FCC), hydrocracking and hydrotreating units in refineries as well as further processing of intermediate products in process units which receive feedstock from upstream process units that simultaneously process biogenic and petroleum feedstocks.

"C14", "14C" or "$^{14}$C" as used herein refers to the isotope of carbon that contain 6 protons and 8 neutrons.

"In situ" as used herein refers to measurement of the C14 renewable content at selected intervals in the co-processing operation to provide rapid results such that ad hoc adjustments may be made to unit operations, targeted blend recipes, bio-feedstock feed rate or any other process parameters on a timely basis at any point prior to and up to the final processed tank.

"Timely basis" as used herein refers to a time period such that there is no detrimental impact to process operations, facility logistics or product distribution. "Scintillation Cocktail" as used herein refers to cocktail mixed with sample to facilitate the detection of C14 radioactive decay.

"CPM" as used herein refers to Counts per minute, the amount of counts that the detector sees per minute.

"DPM" as used herein refers to the true number of decays that occurred in the sample per minute after accounting for background and counting efficiency.

"TDCR" as used herein refers to Triple to double coincidence ratio, the ratio of counts detected by 3 detectors over the number of counts that were detected my 2 detectors.

"Delay Time" as used herein refers to the time the instrument waits after method is started to start counting.

"Counting Time" as used herein refers to the actual time used to count decays in the sample, is dictated by either set counting time or the max number of counts, whichever is quicker.

"Beta decay" as used herein refers to the release of an electron during radioactive decay, the beta decay from C14 does not pose a danger to humans in this application.

"Wipe Test" as used herein refers to a test that is done to determine if a surface has been contaminated with C14.

"C14 Spike Standard" as used herein refers to a standard prepared to spike into samples to measure counting efficiency.

"QC standard set" as used herein refers to a set of standards used to make sure the instrument is operating correctly.

Co-processing refers to the simultaneous transformation of biogenic feedstocks and intermediate petroleum products such as vacuum gas oil (VGO) in existing petroleum refinery process units to produce renewable hydrocarbon fuels. Co-processing involves cracking, hydrogenation, or other processing of semi-processed biogenic oils, vegetable oils and fats in combination with petroleum intermediates to obtain finished fuels such as diesel, gasoline, and jet fuels. Some co-processing operations may include further processing of intermediates containing biogenic carbon from the primary co-processing plant in order to obtain finished fuels or blendstocks.

Co-processing in FCC units is a promising method of transforming pyrolysis oil and other biogenic feedstocks into renewable fuels. The FCC unit provides an environment for cracking heavier molecular weight pyrolysis oil, as it is more selective and can be carried out under milder reaction conditions. Catalytic cracking removes oxygen present in feedstocks in the form of water, CO and CO2 via simultaneous dehydration, decarboxylation, and decarbonylation.

Providing quantification of renewable C14 carbon content in the above-mentioned large-scale operations while lowering the limit of detection enables a demonstration of compliance with LCFS carbon intensity standards more efficiently.

Previous methods of bio-based carbon quantification encompass accelerator mass spectrometry (AMS) radiocarbon analysis of liquid fuels which yields a limit of detection of 0.4 wt % (*Fuel*, Vol. 237, February 2019) for bio-based carbon content. Additionally, a problem in the state of the art has been that C14 methods currently utilized may not be applicable to low blending levels particularly in FCC units (Co-processing in Petroleum Refineries: CARB 5$^{th}$ Work Group meeting, Oct. 19, 2018).

An embodiment of the method disclosed herein is a method of monitoring renewable carbon in fuel streams in a refinery, while co-processing a bio-feedstock with a fossil feedstock comprising: a. blending bio-feedstocks include pyrolysis oil from pyrolysis, and triglycerides such as virgin vegetable oils, used cooking oils, fat-based oils, and primary bio-feedstocks such lignin and sugars; b. refining the blended bio-feedstocks using processes that include but are not limited to (1) thermal cracking such as vis breaking and coking, (2) catalytic cracking, (3) hydrotreating, and (4) hydrocracking; c. measuring renewable carbon content in the refinery streams and products; d. determining the total renewable fuels produced wherein greater than 90% of renewable carbons produced during the co-processing are accounted for.

Figure 2:
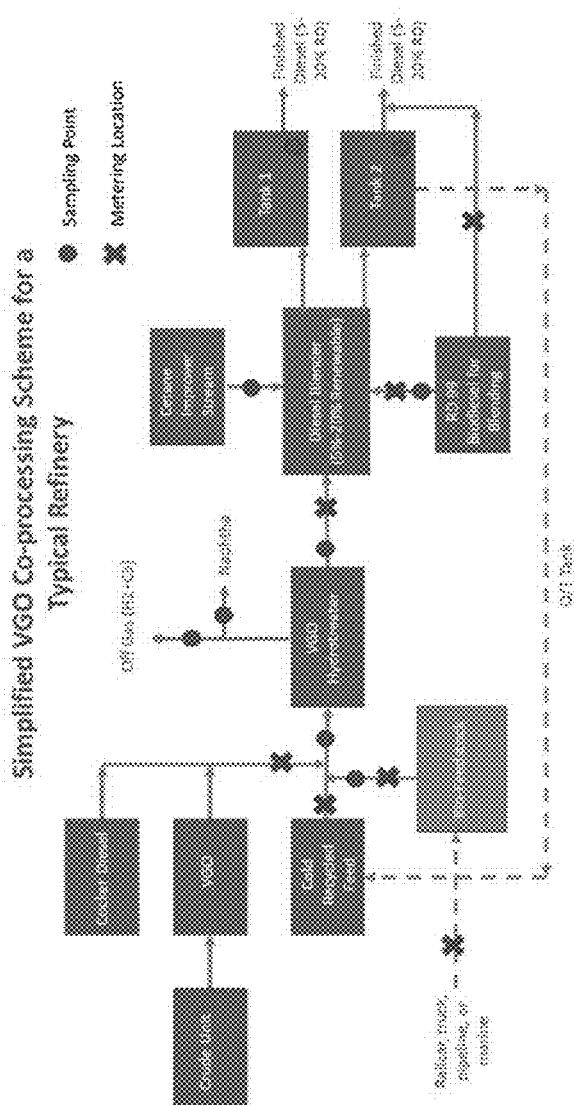
FIG. 2 is a simplified VGO co-processing scheme with sampling points and metering locations for a typical fuel refinery.
Figure 3:
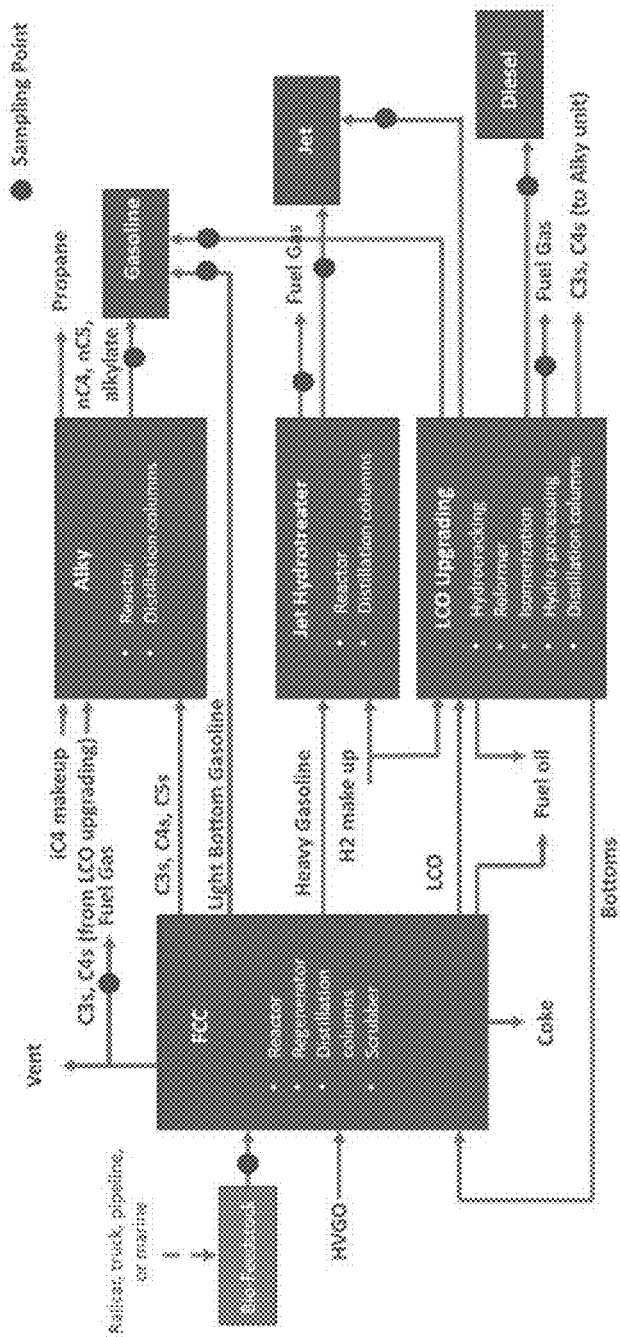
FIG. 3 is a simplified FCC co-processing scheme with sampling points for a typical fuel refinery

Another embodiment is the use of fixed sampling points within a coprocessing operation and analyzing renewable carbon content in the samples in part using radiocarbon analysis. The sampling points reduce the total number of downstream measurements typically required when determining bio-based carbon content in a refinery co-processing petroleum and bio-based feedstocks. FCC co-processing carbon sampling points as detailed in FIG. 3 comprise Initial bio feedstock input into FCC. FCC to fuel gas and FCC to gasoline—specifically via light bottom gasoline; light cycle oil (LCO) upgrading unit to fuel gas, diesel, Jet and gasoline; jet hydrotreater to fuel gas and jet; alky unit to gasoline. VGO co-processing carbon sampling points as detailed in FIG. 2 comprise bio feedstock introduction to cold recycled feed (CRF) and combined CRF bio feedstock input to VGO hydrotreater; VGO hydrotreater output to off gas, naphtha and diesel blender; diesel blender to finished diesel; cetane improver stream to diesel blender; renewable diesel 99 to diesel blender.

A preferred embodiment is the use of an automated triple-to-double coincidence ratio (TDCR) scintillation counter to determine renewable carbon content in the refinery liquid feedstocks and products. An even more preferred embodiment is the use of a HIDEX LSC. Table 3 below shows the 14C activity as determined by various vegetable oil feedstocks using the TDCR liquid scintillation counter and optimized analysis parameters. Each sample was analyzed for three times and Standard Deviation was determined. The 14C radiocarbon decay was measured as Disintegrations per Minute (DPM). Table 1 demonstrates biobased carbon content results for various blends of Aviation Turbine Jet fuel (Tank 1) and renewable diesel A. Each sample was analyzed for five times and Standard Deviation was determined using the automated triple-to-double coincidence ratio (TDCR) liquid scintillation counter.

A further embodiment of the invention is a method of adjusting renewable carbon content by measuring the amount of C14 present in hydrocarbon fuels and their blend streams in a FCC or VGO coprocessing operation by 1) providing fixed sampling points within the petroleum coprocessing operation between input of bio feedstock to select product outputs and 2) analyzing the samples collected in situ using C14 analysis, 3) determining the total renewable content from the collected samples and 4) adjusting the determined renewable content by blending with a renewable carbon source or by increasing the feed rates of the renewable stream to the coprocessing operations.

For example, in an operation wherein the renewable content is soybean oil targeted for co-processing at 5%, wherein the final fuel is expected to have 5% renewable content for a pipeline specification. If C14 analysis as described herein shows that the final fuel only has 4% renewable carbon, then additional renewable diesel can be blended into the co-processed product. This maximizes the renewable credits the refinery can generate. Another option is to increase the amount of soybean oil being fed to the unit, so that the final fuel renewable carbon content increases to 5%. The method as described herein can be applied to any partially renewable fuel and any renewable content target whether for optimization or for compliance with specifications or regulations, including but not limited to gasoline, jet, diesel, gasoils, fuel oil or LPG.

A further embodiment of the invention is utilizing C14 measurement at strategic points in refineries or blend facilities wherein renewable and petroleum products are processed singularly or in combination to produce a final biofuel product with a maximized C14 content from either coprocessing or blending operations. Maximized C14 content as used herein describes achieving a C14 content within a biofuel product which generates a maximum of renewable credits including but not limited to RINS, LCFS credits and associated accounting programs for renewable content or desired percentage of renewable content or maximizing to a specification such as federal labeling requirements or otherwise. Strategic points and environments within these processing environments include but are not limited to: 1) settled tanks containing renewable components such as but not limited to renewable diesel tanks wherein there has been cross contamination of a petroleum product used upon transfer of the renewable product to the renewable tank such as contamination of renewable diesel with fossil diesel; 2) blend component tanks in refineries blending multiple components to create a final fuel; 3) intermediate streams in the co-processing of renewable feedstocks and 4) intermediate streams of refineries blending multiple components to create a final fuel. Examples of these embodiments within these environments are described below. The method as described herein employs sample collection from these strategic points or environments with vessels of appropriate size that are not capped with a cellulosic, lignin, polysaccharide or carbonaceous material that may factor into the accounting of C14 renewable content.

EXAMPLE 1

Refineries or blend facilities which handle both renewable and petroleum products have high probability of cross-contamination. One example includes unloading renewable diesel off a cargo ship through a wharf connection, or pushing renewable diesel through intra-facility pipelines. In order to fully transfer the renewable diesel to the facility's tank, petroleum diesel is often used to push the fluid through the pipeline. In order to ensure 100% of the renewable diesel is transferred to the tank, some petroleum diesel must be pushed into the tank as well. This results in petroleum volumes commingling in the renewable diesel tank. Although the purchased renewable diesel is 100% renewable, the renewable diesel tank will contain petroleum content which reduces the renewable percentage below 100%. By applying a fixed sampling point at the tank and conducting in situ C14 testing using the method described in the patent after the tank has been settled, an accurate measurement of the C14 content can be achieved. This accurate measurement will allow for extra volume from the (partially) renewable diesel tank to be blended into the final diesel blend or directly into the diesel pipeline while still meeting product specifications. For example, if the product specification is 5% maximum renewable diesel content and the renewable diesel tank is determined to contain 90% renewable content, 5.6% by volume may be blended from the mostly renewable diesel tank while still meeting the 5% renewable content target.

EXAMPLE 2

Refineries blend multiple components to create a final fuel. When co-processing, biogenic carbon will end up across multiple products and tanks. Economics and natural process variation cause refinery yields to change. This means that a given blend component will see varying C14 content. By applying a fixed sample point at the blend component tanks and measuring C14 content using the in situ method described above, the blend recipes may be changed in order to maximize C14 content of a specific blend. In this way, a blender might choose to blend 10% of a component to optimize C14 content where normally they would blend 5% to meet a fuel specification.

EXAMPLE 3

When co-processing renewable feedstocks, different biogenic content will end up in different boiling point ranges. By testing the intermediate streams, the refinery could choose to change the operating parameters in a process unit such as but not limited to adjusting the temperatures in a distillation column or reactor in order to maximize the C14 concentration in a stream that has more value.

EXAMPLE 4

Refineries blend multiple components to create a final fuel. When co-processing, biogenic carbon will end up across multiple products and tanks. Economics and natural process variation cause refinery yields to change. By testing the intermediate streams using the in situ method described above, the refinery could choose to vary the biogenic lipid feed rate to a process unit in order to control the C14 content of the blend components or final products.

TABLE 1

Aviation Turbine Jet Fuel Tank 1 and Renewable Diesel A

| Sample | Measured wt. % Biobased Carbon (1) | Measured wt. % Biobased Carbon (2) | Measured wt. % Biobased Carbon (3) | Measured wt. % Biobased Carbon (4) | Measured wt. % Biobased Carbon (5) | Average wt. % Biobased Carbons | Standard Deviation |
|---|---|---|---|---|---|---|---|
| 1 | 0.13 | −0.17 | 0.58 | 0.37 | 0.15 | 0.21 | 0.28 |
| 2 | 0.43 | 0.99 | 1.07 | 0.66 | 0.99 | 0.83 | 0.22 |
| 3 | 0.84 | 0.67 | 0.94 | 0.9 | 1.26 | 0.92 | 0.22 |
| 4 | 2.07 | 2.31 | 1.47 | 2.08 | 2.15 | 2.02 | 0.32 |
| 5 | 2.17 | 2.62 | 2.98 | 2.52 | 2.22 | 2.50 | 0.33 |
| 6 | 3.20 | 3.37 | 2.8 | 2.92 | 3.15 | 3.09 | 0.23 |
| 7 | 5.57 | 5.18 | 5.42 | 5.63 | 5.7 | 5.50 | 0.20 |
| 8 | 9.94 | 9.93 | 10.3 | 10.24 | 10.33 | 10.15 | 0.20 |
| | | | Average Standard Deviation | | | | 0.26 |

Table 2 demonstrates bio-based carbon content results for various blends of Aviation Turbine Jet fuel (Tank 2) and renewable diesel A. Each sample was analyzed for five times and Standard Deviation was determined using the automated triple-to-double coincidence ratio (TDCR) liquid scintillation counter.

TABLE 2

Aviation Turbine Jet Fuel Tank 2 and Renewable Diesel A

| Sample | Measured wt. % Biobased Carbon (1) | Measured wt. % Biobased Carbon (2) | Measured wt. % Biobased Carbon (3) | Measured wt. % Biobased Carbon (4) | Measured wt. % Biobased Carbon (5) | Average wt. % Biobased Carbons | Standard Deviation |
|---|---|---|---|---|---|---|---|
| 1 | 0.24 | 0.21 | 0.68 | 0.82 | 0.85 | 0.56 | 0.31 |
| 2 | 0.99 | 1.71 | 1.37 | 1.81 | 1.93 | 1.56 | 0.38 |
| 3 | 1.56 | 1.57 | 2.01 | 1.74 | 1.96 | 1.77 | 0.21 |
| 4 | 1.45 | 1.74 | 2.23 | 2.49 | 2.11 | 2.00 | 0.41 |
| 5 | 2.51 | 2.27 | 2.75 | 2.88 | 2.5 | 2.58 | 0.24 |
| 6 | 2.96 | 3.02 | 3.04 | 3.26 | 3.31 | 3.12 | 0.16 |
| 7 | 5.32 | 5.28 | 5.28 | 5.87 | 5.66 | 5.48 | 0.27 |
| 8 | 11.07 | 10.13 | 10.62 | 10.37 | 10.48 | 10.53 | 0.35 |
| | | | Average Standard Deviation | | | | 0.29 |

TABLE 3

| No. | Sample | Run 1 DPM/g Carbon | Run 2 DPM/g Carbon | Run 3 DPM/g Carbon | Run 4 DPM/g Carbon | Standard Deviation |
|---|---|---|---|---|---|---|
| 1 | Soybean Oil 1 | 12.45 | 12.49 | 12.34 | 12.43 | 0.08 |
| 2 | Soybean Oil 2 | 12.63 | 13.19 | 12.51 | 12.78 | 0.36 |
| 3 | Canola Oil 1 | 12.07 | 12.2 | 12.52 | 12.26 | 0.23 |
| 4 | Soybean Oil 3 | 13.34 | 12.99 | 13.03 | 13.12 | 0.19 |
| 5 | Canola Oil 2 | 12.2 | 12.83 | 12.36 | 12.46 | 0.33 |
| 6 | Canola Oil 3 | 12.4 | 13.06 | 12.36 | 12.61 | 0.39 |
| 7 | Soybean Oil 4 | 13.18 | 14.02 | 13.18 | 13.46 | 0.48 |
| 8 | Canola Oi 4 | 12.61 | 13.32 | 12.83 | 12.92 | 0.36 |
| | Average Standard Deviation | | | | | 0.30 |

For carbon-bearing refinery gas, such as fuel gas, accelerator mass spectrometry (AMS) may be used to determine renewable carbon content as described by ASTM D-5291. Table 4 demonstrates the carbon content of the feedstocks and product streams as determined by method ASTM D-5291. Table 5 shows quantifying the closeness of agreement between bio-based carbon content as determined by using the automated triple-to-double coincidence ratio (TDCR) liquid scintillation counter and using the accelerator mass spectrometry (AMS).

TABLE 4

| No. | Sample Feedstock | Sample Product Stream | Carbon Content, wt. % CHN Analysis (ASTM D5291) |
|---|---|---|---|
| 1 | Soy Oil 1 | | 77.9 |
| 2 | Soy Oil 2 | | 78.3 |
| 3 | Canola Oil 1 | | 78.27 |
| 4 | Canola Oil 2 | | 79.51 |
| 5 | Soy Oil 3 | | 77.97 |
| 6 | Canola Oil 3 | | 78.26 |
| 7 | Soy Oil 4 | | 77.92 |
| 8 | | Renewable Diesel 1 | 85.42 |
| 9 | | Renewable Diesel 2 | 85.92 |
| 10 | | Refinery Stream 1 | 84.38 |
| 11 | | Refinery Stream 2 | 86.96 |
| 12 | | Refinery Stream 3 | 87.43 |

TABLE 5

| Sample | TDCR-LSC Averaged Bio-based Carbon, wt. % | AMS Averaged Bio-based Carbon, wt. % |
|---|---|---|
| 1 | 0.56 | 0.51 |
| 2 | 1.56 | 1.11 |
| 3 | 1.77 | 1.56 |
| 4 | 2.00 | 2.14 |
| 5 | 2.58 | 2.57 |
| 6 | 3.12 | 3.39 |
| 7 | 5.48 | 5.72 |
| 8 | 10.53 | 10.18 |
| Coefficient of correlation | | 0.997 |

The method as described herein provides a limit of detection of about 2.0 wt % to about 0.7 wt % for bio-based carbon content when calculated as three times the standard deviation. This lower detection limit can provide more accurate measurements at low blending levels thus solving the aforementioned problem in the state of the art. Potential Systematic Error in the sample preparation and measurements was removed by applying a Bias Correction (Blank Correction) after comparing the results between the TDCR Scintillation Counter and AMS, ASTM D-6866-18, wherein the Bias Correction is either constant correction, proportional correction, or a linear correction which is a combination of proportional and constant. Additionally, the precision for the method, when expressed as Repeatability, and is a quantitative expression for the random error associated with the difference between two independent results and expressed as two times standard deviation at the 95% confidence interval, is <1.0 wt. %, preferably <0.8 wt. %.

METHOD

Samples from the sampling locations set forth above for FCC and VGO coprocessing (fuels, their component streams, and bio feeds) are mixed with the Maxilight scintillation cocktail and placed into the Hidex 300SL instrument. The instrument is then used to determine the C14 decay rate in the sample to determine the bio carbon content of the sample. The instrument will then export an excel file with the measured bio carbon content of the sample. The specific method steps comprising sample preparation, sample analysis and calculation are set forth below.

A. Sample Preparation
Background Samples.
1) Gather samples from each proposed sampling points that have no bio carbon present (10-18 mL).
   TK 491 LABS (Low Aromatic Jet).
   TK 493 Isomac Combined Jet (Unhydro).
   TK 494 NHT3 Jet.
   TK 991 (gasoline).
   VGO ALAD Diesel.
2) Weigh out 10 mL of each sampling point and blends that will need to be analyzed for bio carbon content into 20 mL low background vials using pipettes and the analytical balance. Necessary samples include:
   TK 491 LABS (Low Aromatic Jet).
   TK 493 Isomac Combined Jet (Unhydro).
   TK 494 NHT3 Jet.
   TK 991 (gasoline).
   VGO ALAD Diesel.
   80% VGO ALAD Diesel+20% TK 491 LABS (Low Aromatic Jet).
   50% TK 493 Isomac Combined Jet (Unhydro) 50% TK 494 NHT3 Jet.
3) Record the weights of each of the samples used and label each vial cap with what sample was placed in each along with the date the sample was made—avoid writing on the glass of the vial as this will interfere with the instrument detection.
4) Add 10 mL of MaxiLight solution to each sample.
5) Cap all vials and shake well.
6) Place vials into the Hidex 300SL auto sampler tray, allow samples to sit in the tray for 1.5 hours before running (this delay will be set in the software).
7) If this is the very first time running backgrounds repeat steps 2-7 four more times to start the rolling 5 background average that will be continued each time backgrounds are remade and run.
8) These blanks will need to be remade and measured on a yearly basis to make sure same background levels are being measured.
9) Feed Samples.
10) C14 Spike Standard.
11) Place 2 capsules from the Internal Standard Kit C14—Organic into one of the 20 mL low background vials.
12) Mix 4 mL of toluene with the capsules and mix well. Allow the toluene to dissolve the analyte for 30 minutes before proceeding. Once mixed, label the vial cap "toluene spike standard" along with the date it was made (DO NOT write on the glass of the vial as this will interfere with the instrument detection). This sample will be used to spike samples later and should be stored in the Hidex 300SL auto sampler or in a dark dry location. Sample will last until depletion.
13) C14 Spike Activity Standard. Add 20 mL of Maxilight solution (two 10 mL pumps) into a 20 mL low background vial. Weight out 50 uL of the C14 Spike standard from step 10. Record the weight of the spike. This sample is used to determine the activity of the C14 spike standard and should be remade every month or when a new C14 spike standard is made.
14) Samples. Weigh out two 10 mL aliquots of each sample into two different 20 mL low background vials using the pipettes on the analytical balance. Record weights of sample used. Add 10 mL of Maxilight solution to each sample. Cap both vials and shake well. Once mixed, label the vial cap with sample name along with the date it was made (DO NOT write on the glass of the vial as this will interfere with the instrument detection). Take one of the two samples to the designated spiking area and spike the sample with 50 uL of C14 spike standard, record the weight of the spike.

Reshake up the spiked sample, once mixed, denote that this sample is the one that was spiked (DO NOT write on the glass of the vial as this will interfere with the instrument detection).

Place both vials into the Hidex 300SL auto sampler tray with the spiked sample being to the right of the unspiked sample allow samples to sit in the try for 1.5 hours before running (this delay will be set in the software).

B. Hidex 300SL Sample Analysis Procedure

Place vials into the auto sampler try of the Hidex 300SL. Make sure to denote what samples went into what positions of the tray. Start at position A01 and proceed left to right filling the rack without skipping a position. If more than 8 samples are used start the next row at position B01.

Open MikroWin 300SL software, click this icon on the desktop. Open Template, click this icon in the MikroWin 300SL software. Select Sample Analysis Template. Edit Tray ID from YYYMMDD-##to YYYYMMDD-Background Samples.

Name Samples as desired to make it clear what sample point or blend that is being analyzed, under Measurement>Tray Data>Sample Identifiers, in the upper left side menu in the MikroWin 300SL software. Make sure the name matches the position it was put in on the auto sampler.

If Sample ID box is grayed-out, select Edit>Reset followed by turning cooling on Instrument>Cooling On and repeat steps from "Open Template".

Start the instrument by clicking the green arrow button. The method is set to scan each sample for 5 hours. Once the instrument is finished running an excel file will then be automatically exported into this file directory, C:\ProgramData\MikroWin 300SL\Transfer. Open the exported excel file and look at cell CPM column and write this number down next to that sample in the logbook. This number needs to be incorporated into the rolling average that is being used to determine the background CPM level for each stream. Average this number with the previous four background measurements that were taken on that stream and use this number as the background value for each of the sample streams.

If this is the first-time running background samples this should be done a total of 5 times, once for each of the backgrounds. The 5 background measurements need to be averaged to be used later for background of sample information.

B(1). Sample Analysis—This is to be done for all liquid samples to be analyzed for bio carbon content. Place vials into the auto sampler try of the Hidex 300SL. Make sure to denote what samples went into what positions of the tray. Start at position A01 and proceed left to right filling the rack without skipping a position. If more than 8 samples are used start the next row at position B01.

The spiked version of every sample should be placed immediately to the right of the unspiked sample, i.e. unspiked in A01 with spiked in A02.

Open MikroWin 300SL software, click this icon on the desktop. Open the Organizer, click this icon in the MikroWin 300SL software.

Fill out the following information for each of the samples making sure that the information for each sample is matched with the correct position.

Sample ID—should be easily matched to sampling location and should have a sampling date associated with it.

Templatefile—select the "Sample Analysis Template" for all samples and spiked samples.

Sample Weight—amount of sample pipetted into the vial.

C14 Spike weight—only input a number for those samples that were spiked.

C14 Spike DPM/mg—only input a number for those samples that were spiked, this is the number that was calculated 14.4.9 (this number is to be kept constant until the next C14 spike activity standard is made, once a month or when the C14 spike standard is remade)

Carbon %—determined by CHN measurement. This should be measured for every sample.

Background—should be specific to the fuel or fuel stream that is being measured.

These are the numbers that were measured in 14.2 and should be held constant until new backgrounds are measured, once a year) This background will be a rolling average of the last 5 measurements.

DPM/g Feed—this is the number is determined from 14.3 and will be calculated by software and exported in excel file.

Enter a Tray ID in the following format "YYYYMMDD-SampleAnalysis" (no spaces). Click the "Save Tray" button at the bottom of the Organizer window. Click the "Run Tray" button at the bottom of the Organizer window. Another Window will pop up. Click "Toggle Mode" then click "Run Batch".

Once the instrument is finished running an excel file will then be automatically exported into this file directory, C:\ProgramData\MikroWin 300SL\Transfer.

Open the exported excel file. There will be a row for each sample with one of the cells stating the bio carbon percent of the sample. This is the number to be reported to CARB and EPA.

An image of an example of the exported excel file will be added as FIG. 7 at a later date once software template is set up.

C. Calculations 1.1 How to calculate DPM/g for the feed. This will be calculated by the instrument but here is how to do it by hand if needed or desired.

$$\frac{DPM}{g \ Carbon}$$

$$DPM = \frac{(CPM - Background)}{Efficiency}$$

$$Efficiency = \frac{Measured \ CPM/mg \ of \ Spiked \ Sample - CPM \ of \ Regular \ Sample}{Theoretical \ DPM/mg \ of \ Spiked \ Sample}$$

$$g \ Carbon = g \ sample \times \% \ Carbon$$

1.1.1 CPM is directly measured but the instrument and will be in the output file.

1.1.2 Background will be indirectly determined at RTC and held constant using the feeds that are currently on hand. This will have to redetermined if a feed other than RBD soy is used.

1.1.3 Procedure currently in use is the dissolve the feed 1:10 in a hydrocarbon sample that the background is known and calculating the DPM/g for this sample then using that DPM/g number to back calculate what the background is for the pure feed. Once this is shown to work well it will be formally added to SOP in Section 14.3.

1.1.4 Measured CPM/mg is determined by taking the CPM of the spiked feed sample and dividing it by the mg of spike that was used.

1.1.5 Theoretical DPM/mg was that number calculated in section 14.4.9.

1.1.6 g of sample is the amount of sample that was weighed into the vial.

1.1.7% Carbon is determined by CHN analysis of the sample.

1.2 How to calculate DPM/mg for the C14 standard spike solution (this is calculated in section 14.4.9).

$$\frac{DPM}{\text{mg Spike Solution}} = \frac{(DPM \text{ in Exported Excel File})}{\text{mg of } 14C \text{ Spike Solution Used}}$$

1.3 How to calculate bio carbon percent for the sample. This will be calculated by the instrument but here is how to do it by hand if needed or desired.

$$\frac{DPM \text{ Sample}}{\text{g Carbon Sample}} \div \frac{DPM \text{ Feed}}{\text{g Carbon Feed}} \times 100 = \text{Bio Carbon \% of Sample}$$

1.3.1 DPM Sample/g Carbon Sample is calculated almost exactly like DPM Feed/g Carbon Feed except the backgrounds determine in Section 14.2.

We claim:

1. A method of monitoring renewable carbon in fuel streams in a refinery, while co-processing a bio-feedstock with a fossil feedstock comprising:
   a. Blending bio-feedstocks comprising pyrolysis oil from pyrolysis and triglycerides and primary bio-feedstocks;
   b. Refining the blended bio-feedstocks using processes comprising (1) thermal cracking such as visbreaking and coking, (2) catalytic cracking, (3) hydrotreating, and (4) hydrocracking;
   c. Measuring renewable carbon content in the refinery streams and products selected from the group consisting of the following streams: Fluid Catalytic Cracking to fuel gas and Fluid Catalytic Cracking to gasoline; Fluid Catalytic Cracking to light bottom gasoline; LCO upgrading unit to fuel gas, diesel, Jet and gasoline; jet hydrotreater to fuel gas and jet; alky unit to gasoline; bio feedstock introduction to petroleum feedstock input to diesel hydrotreater; diesel hydrotreater output to off gas, naphtha and diesel blender; diesel blender to finished diesel; cetane improver stream to diesel blender; renewable diesel 99 to diesel blender;
   d. Determining the total renewable fuels produced,
   e. In situ adjustment of the renewable fuels produced in step d with renewable content to attain a desired percentage of total renewable content.

2. The method of claim 1, wherein the triglycerides are selected from the group consisting of vegetable oils, algal oils, used cooking oils, fat-based oils and Fischer-Tropsch waxes derived from the gasification of biomass and the primary bio-feedstock is selected from the group consisting of lignans and sugars.

3. The method of claim 2, wherein the refinery stream metering locations selected such a way that >90% renewable carbons produced during the co-processing could be accounted for.

4. The method of claim 2, wherein the refinery stream samples were collected at locations in the refinery so that >90% renewable carbons produced during the co-processing could be accounted for.

5. The method of claim 4, wherein the number of locations in the refinery were selected so that the total number of samples analyzed are kept being at minimal.

6. The system of claim 2, wherein the analyzer is configured to measure the renewable carbon content based at least in part on radiocarbon analysis.

7. The method of claim 2, wherein the technique used in determining renewable carbon content in the carbon-bearing refinery gas, such as fuel gas, is using the accelerator mass spectrometry (AMS).

8. The method of claim 2, wherein the technique used in determining renewable carbon content in the refinery liquid feedstocks and products is using the automated triple-to-double coincidence ratio (TDCR) scintillation counter.

9. The method of claim 8, wherein the carbon content of the feedstocks and product streams were determined by method ASTM D-5291.

10. The method of claim 8, wherein the precision for the method, when expressed as Repeatability, and is a quantitative expression for the random error associated with the difference between two independent results and expressed as two times standard deviation at the 95% confidence interval, is <1.0 wt. %.

11. The method of claim 8, wherein the Limit of Detection when calculated as three times the standard deviation, is <2.0 wt. %.

12. The method of claim 8, wherein the potential Systematic Error in the sample preparation and measurements was removed by applying a Bias Correction (Blank Correction) after comparing the results between the TDCR Scintillation Counter and AMS (ASTM D-6866-18).

13. The method of claim 12, wherein the Bias Correction is either constant correction, proportional correction, or a linear correction (a combination of proportional and constant).

14. The method of claim 8, wherein the precision for the method, when expressed as Repeatability, and is a quantitative expression for the random error associated with the difference between two independent results and expressed as two times standard deviation at the 95% confidence interval, is <0.8 wt. %.

15. The method of claim 8, wherein the Limit of Detection when calculated as three times the standard deviation, is <1.0 wt. %.

16. The method of claim 2, further comprising C14 measurement at strategic points in refineries or blend facilities wherein renewable and petroleum products are processed singularly or in combination to produce a final biofuel product with a maximized C14 content.

17. The method of claim 15, wherein the strategic point is selected from the group consisting of (1) settled renewable product tanks wherein there has been comingling of a petroleum product used upon transfer of the renewable product to the renewable product tank; (2) blend component tanks in refineries blending multiple components to create a final fuel; (3) intermediate streams in the co-processing of renewable feedstocks and (4) intermediate streams of refineries blending multiple components to create a final fuel.

18. The method of claim 16, wherein the renewable product tank is selected from the group consisting of: renewable diesel or blendstocks thereof, renewable gasoline or blendstocks thereof, renewable jet or blendstocks thereof, renewable gasoil, and renewable liquified petroleum gasses.

* * * * *